(12) United States Patent
Castillo-Garcia

(10) Patent No.: US 9,913,658 B2
(45) Date of Patent: Mar. 13, 2018

(54) MEDICAL DEVICE FOR DEBRIDEMENT OF TISSUE

(71) Applicant: Elvis Castillo-Garcia, Wesley Chapel, FL (US)

(72) Inventor: Elvis Castillo-Garcia, Wesley Chapel, FL (US)

(*) Notice: Subject to any disclaimer, the term of this patent is extended or adjusted under 35 U.S.C. 154(b) by 74 days.

(21) Appl. No.: 15/142,139

(22) Filed: Apr. 29, 2016

(65) Prior Publication Data

US 2016/0242807 A1    Aug. 25, 2016

(51) Int. Cl.
| A61B 17/50 | (2006.01) |
| A61B 17/3207 | (2006.01) |
| A61B 17/00 | (2006.01) |
| A61B 17/32 | (2006.01) |

(52) U.S. Cl.
CPC ......... *A61B 17/320708* (2013.01); *A61B 2017/00438* (2013.01); *A61B 2017/00761* (2013.01); *A61B 2017/320008* (2013.01)

(58) Field of Classification Search
CPC .......... A61B 17/32; A61B 2017/00761; A61B 2017/320004; A61B 2017/320008
USPC ........................................................ 606/131
See application file for complete search history.

(56) References Cited

U.S. PATENT DOCUMENTS

| 2,380,186 | A | 3/1944 | Mayer |
| 2,704,889 | A | 7/1951 | Delinanos |
| 4,703,561 | A | 11/1987 | Parisek |
| 5,659,962 | A | 8/1997 | Tagou |
| D410,112 | S | 5/1999 | Doyle |
| 8,844,080 | B2 * | 9/2014 | Stacy ...................... A47J 43/28 2/163 |
| 8,991,060 | B2 | 3/2015 | Safar |
| 2004/0231167 | A1 * | 11/2004 | Miklos ............... A61B 17/0467 30/298 |

* cited by examiner

*Primary Examiner* — Melanie Tyson
(74) *Attorney, Agent, or Firm* — Thomas Frost

(57) ABSTRACT

In first and second embodiments the device comprises a generally cylindrically shaped body distal end and a proximal end, and is conformed to be received by a fingertip of a medical practitioner. A conical shaped cap is defined at the distal end with a plurality of metal protrusions for debridement scrapping formed on an outer surface, and along a bottom surface of the body. In the alternative second embodiment, a curette styled loop blade with a cutting edge is formed on the bottom surface. A third embodiment does not have the cap and has debridement scrapping protrusions defined along the bottom surface. Straps are attached to the body to secure the device to any finger of a medical practitioner.

2 Claims, 9 Drawing Sheets

FIG. 19

US 9,913,658 B2

MEDICAL DEVICE FOR DEBRIDEMENT OF TISSUE

FIELD OF THE INVENTION

The present invention relates to a medical device for wound debridement, namely the removal of dead, damaged or infected tissue by cutting or by scrapping to assist on the alteration of tissue from chronic phase to acute phase.

BACKGROUND OF THE INVENTION

Debridement is the removal of dead, damaged or infected tissue in wounds to improve the healing of the remaining healthy tissue. Surgical instruments, such as curettes, scalpels, scissors and forceps, are normally used by medical practitioners to debride a wound. These instruments present a disadvantage in that access to the entire area of treatment is limited.

The current invention is directed to a debridement medical device mounted on a forefinger of a practitioner to access areas not available to conventional surgical tools, such as curettes due to their rigid structure. Metal protrusions on a base facilitate mild debridement of a wound in areas that cannot be accessed. Additionally, metallic protrusions on a distal tip facilitate crosshatching thicker eschar (a slough or piece of dead tissue) without having to use a blade.

The current invention is convenient to use due to its ability to access tunnels or tunneled wounds, and wounds with undermining. Time will be saved in healing chronic or acute wounds with dead, damaged or infected tissue.

SUMMARY OF THE INVENTION

The general purpose of the present invention, which will be described subsequently in greater detail, is to provide a new and improved wound debridement medical device.

In a first embodiment the device comprises a generally cylindrically shaped body distal end and a proximal end, and is conformed to be received by a fingertip of a medical practitioner. A conical shaped cap is defined at the distal end with a plurality of metal protrusions for debridement scrapping formed on an outer surface, and along a bottom surface of the body. In an alternative embodiment, a curette styled loop blade with a cutting edge is formed on the bottom surface. A third embodiment has a body with a platform affixed to the bottom of the body, and a plurality of metal protrusions extending vertically.

Straps are attached to the body, and can be comprised of elastic, plastic, rubber or any other resilient and flexible material. The straps are spaced apart and secure the device to any finger of a medical practitioner.

BRIEF DESCPTION OF THE DRAWINGS

Figure 1:
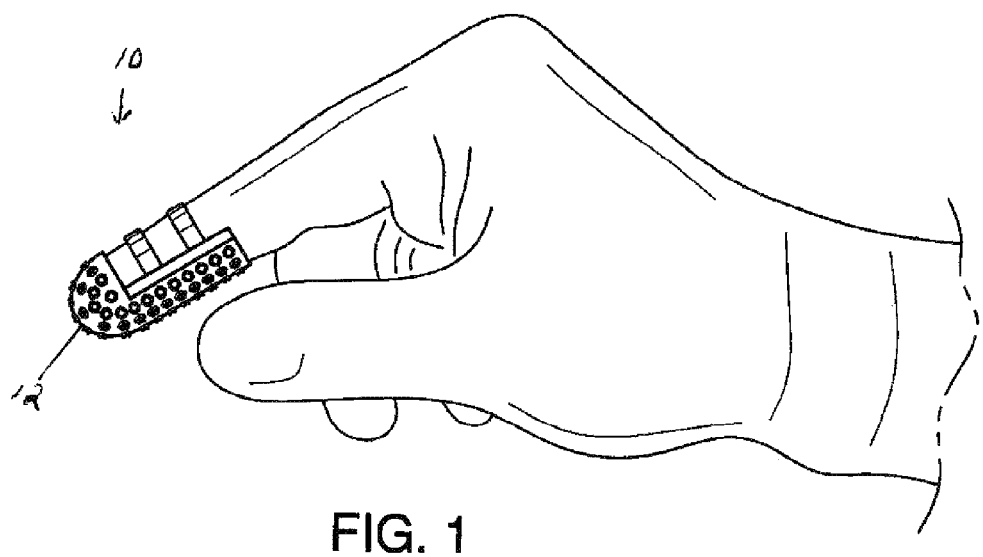

The invention will be better understood and objects other than those set forth above will become apparent when consideration is given to the following detailed description thereof. Such description makes reference to the annexed drawings wherein:

FIG. 1 is a side elevational view of a first embodiment of the present invention mounted on the forefinger of a medical practitioner.

Figure 2:
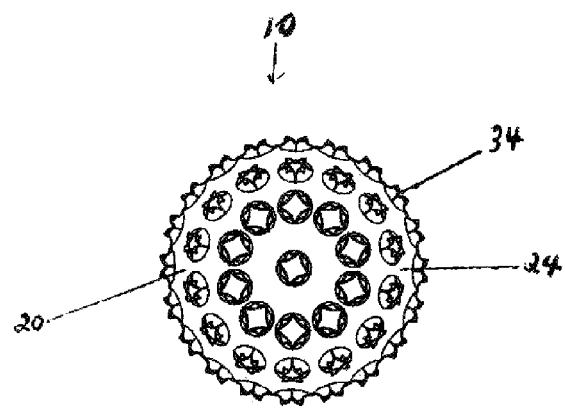
Figure 3:
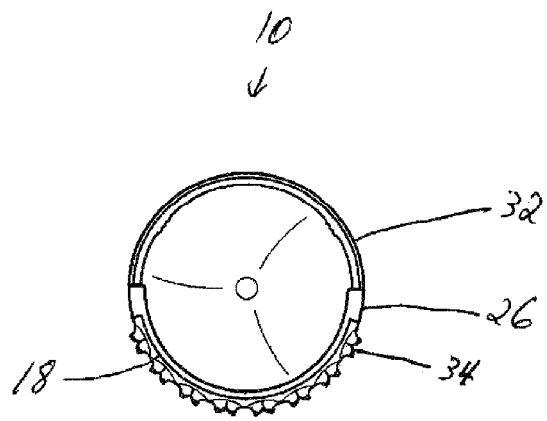
Figure 4:
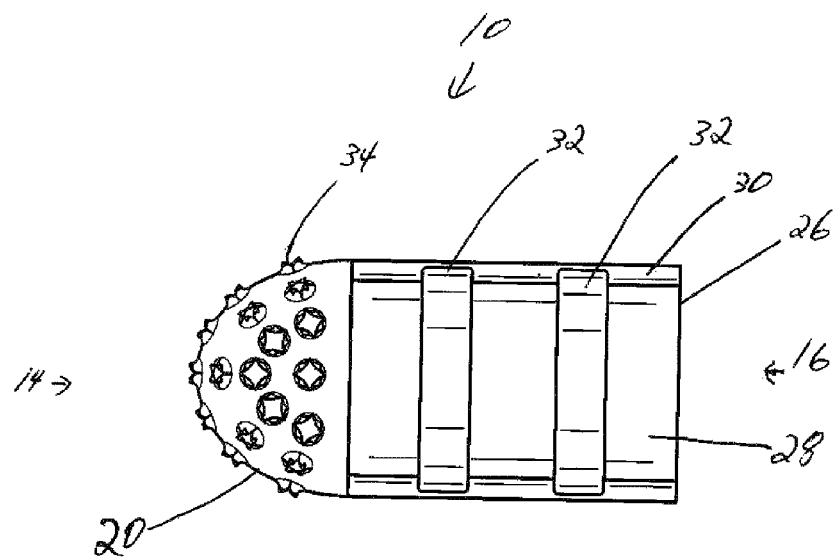
Figure 5:
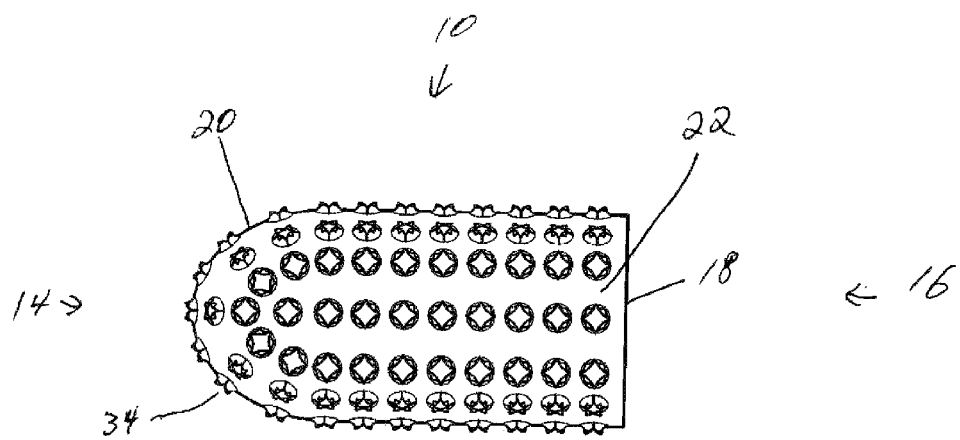
Figure 6:
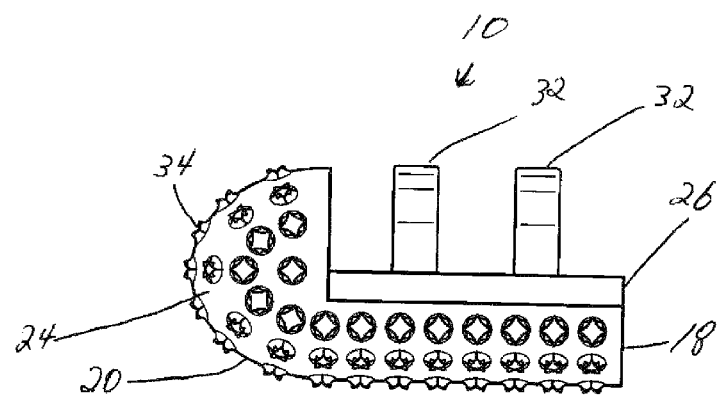
Figure 7:
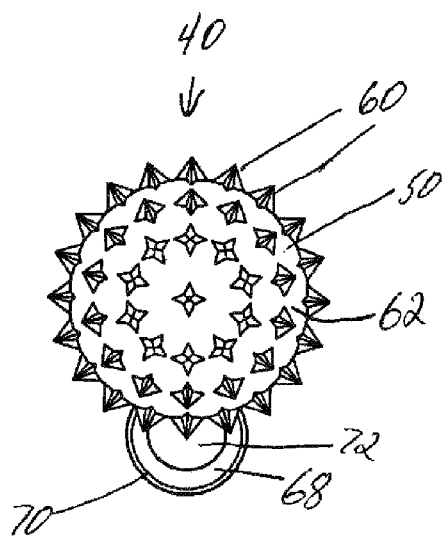
Figure 8:
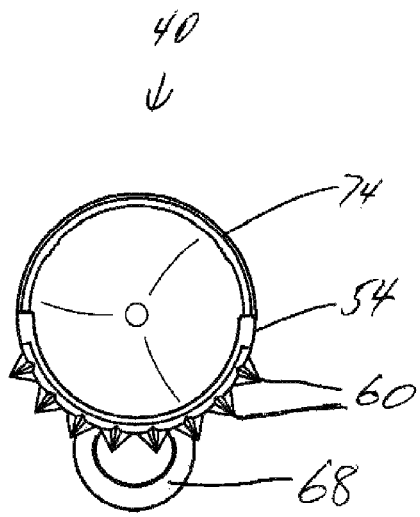
Figure 9:
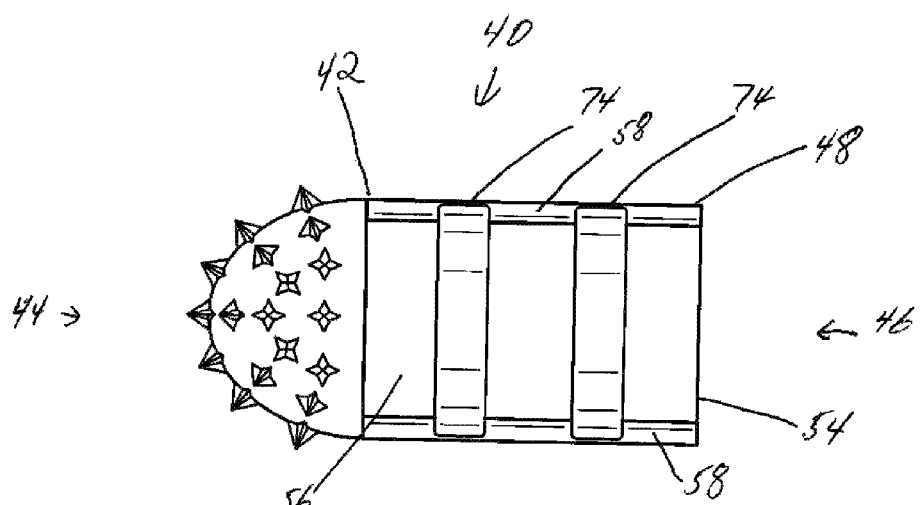
Figure 10:
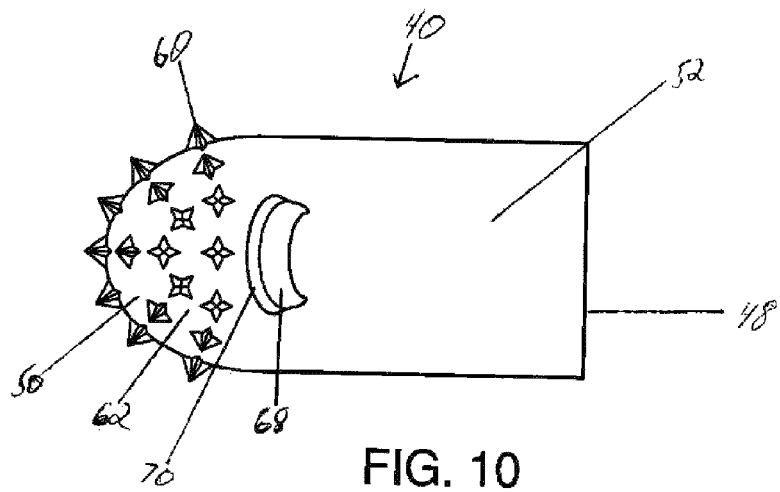
Figure 11:
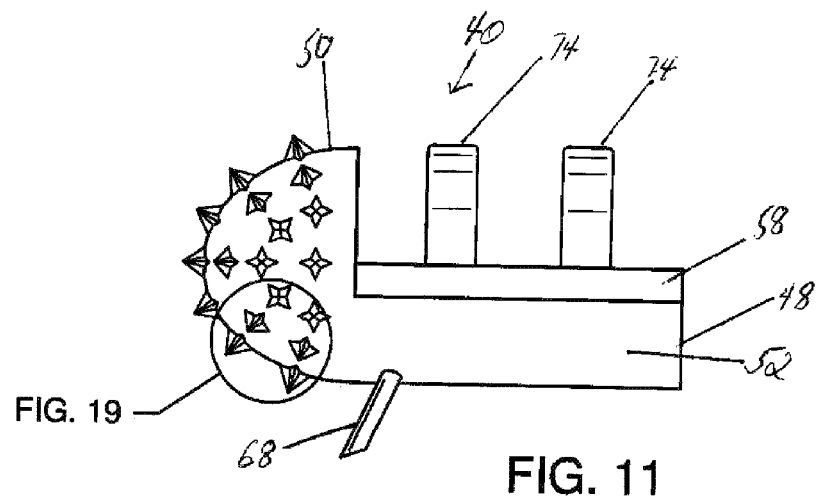
Figure 12:
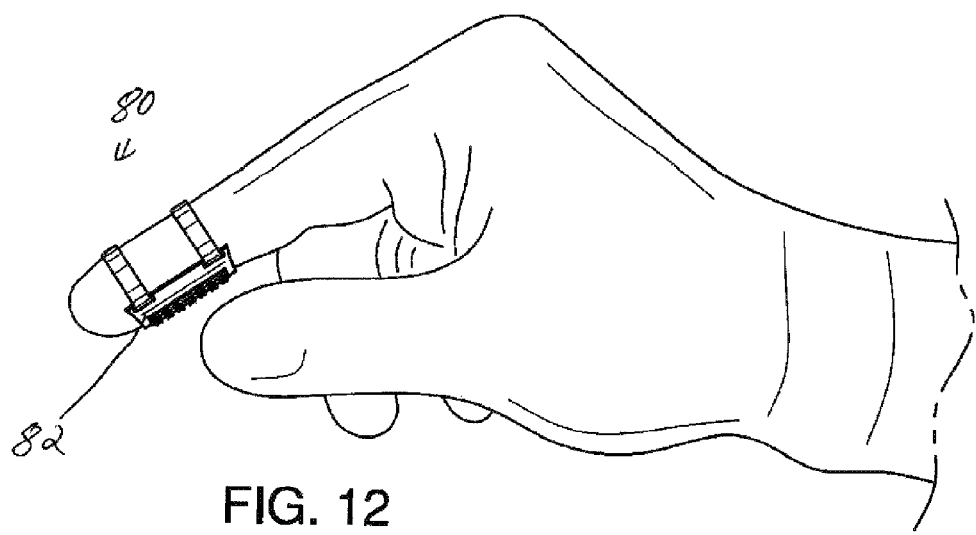
Figure 13:
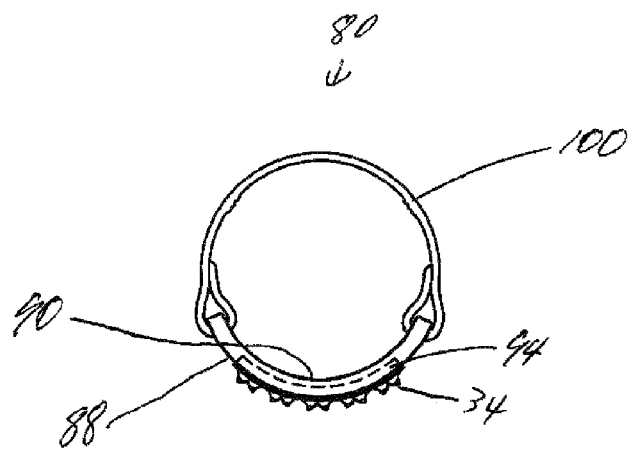
Figure 14:
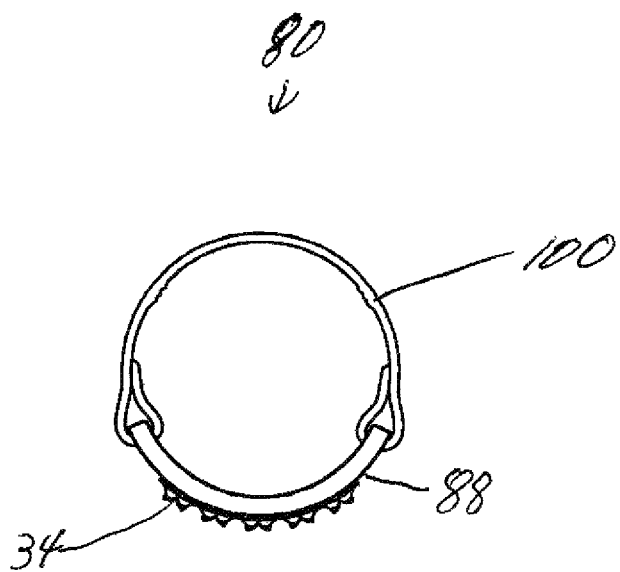
Figure 15:
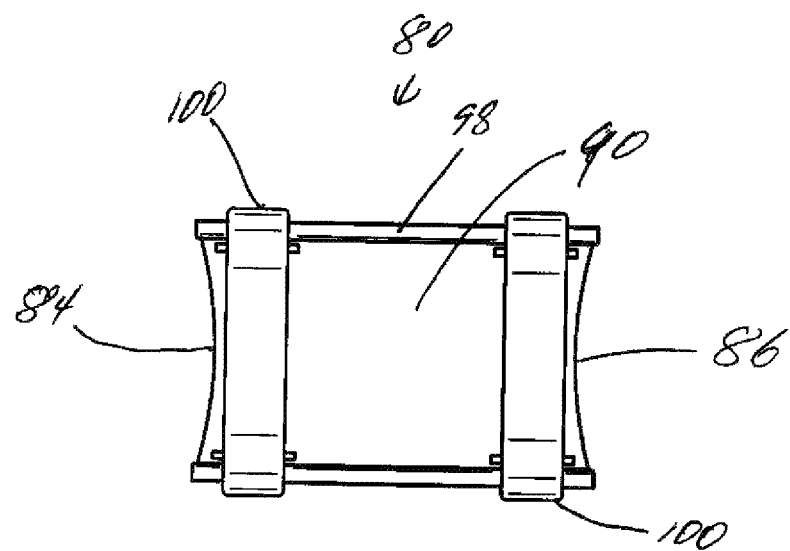
Figure 16:
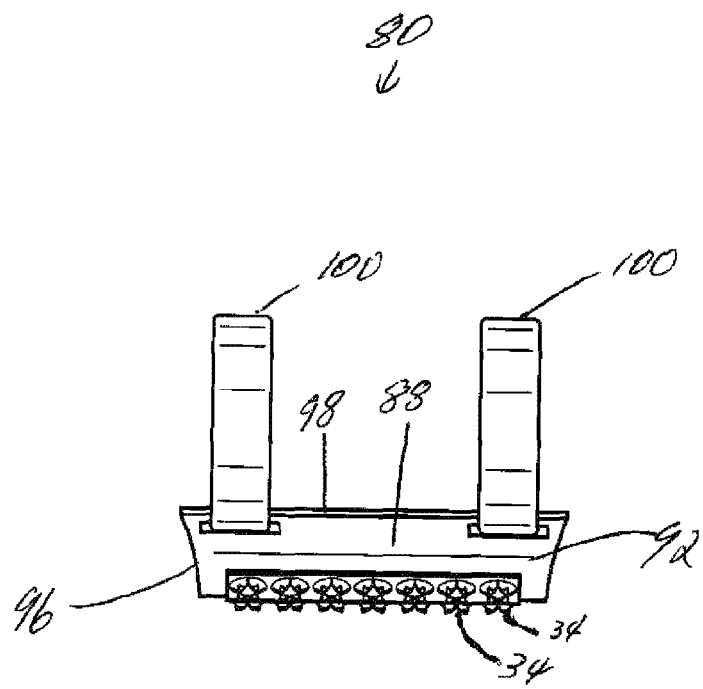
Figure 17:
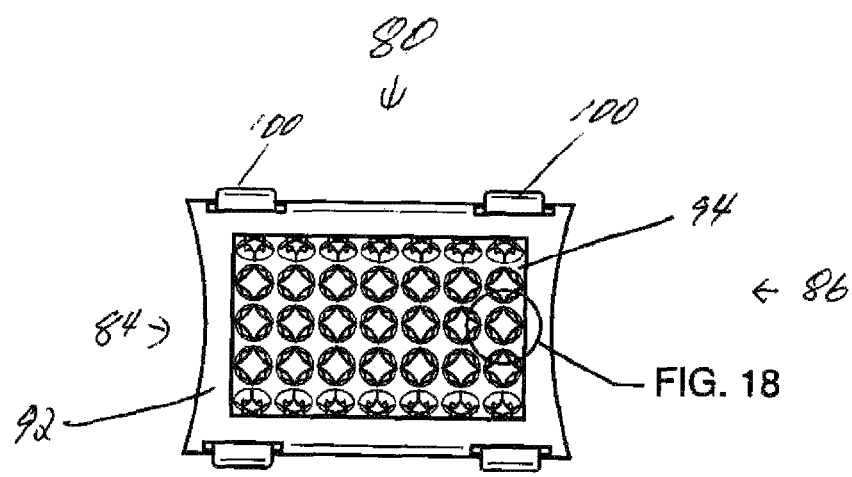
Figure 18:
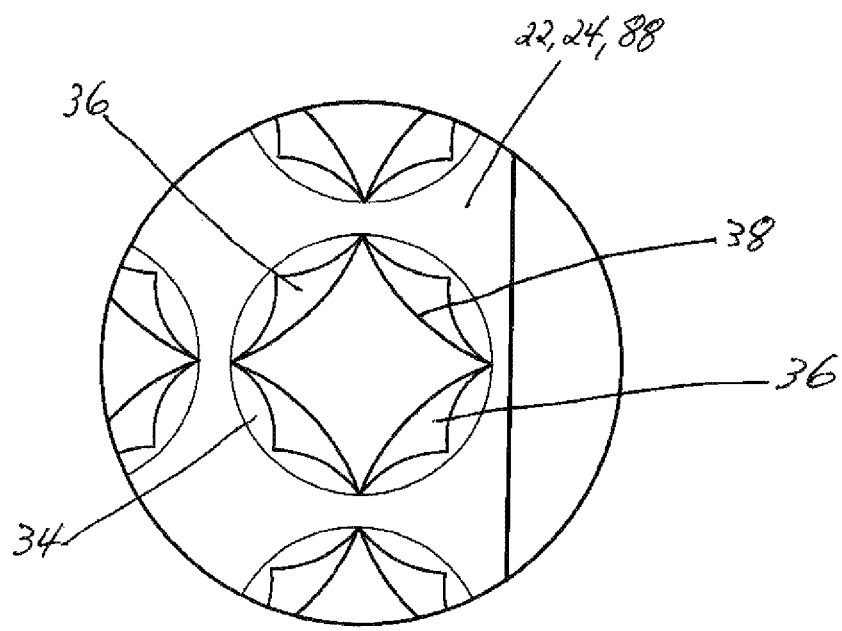
Figure 19:
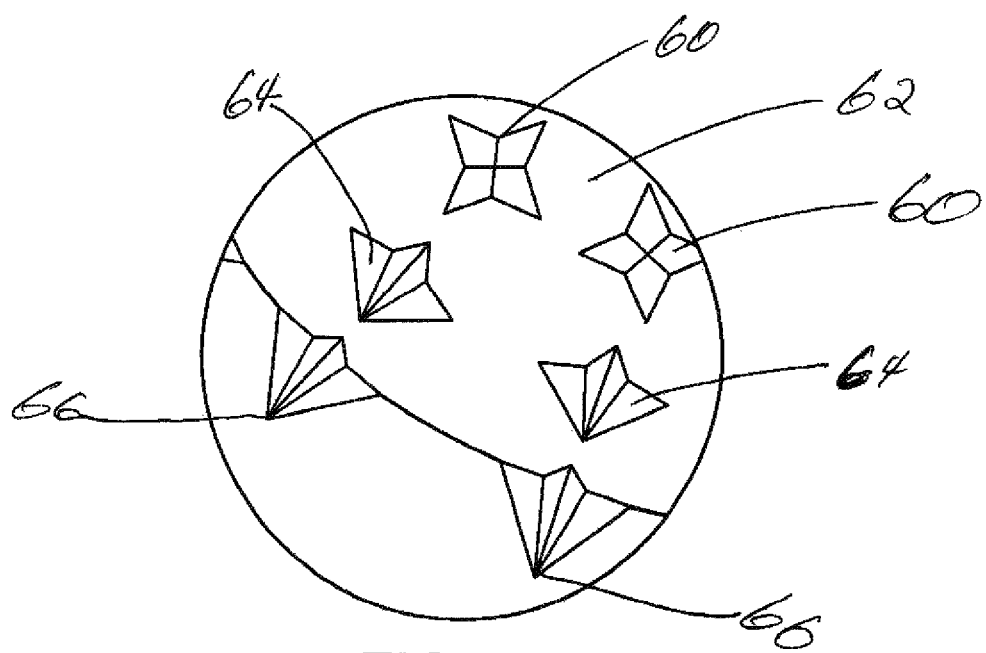

FIG. 2 is a front elevational view of the first embodiment.
FIG. 3 is a rear elevational view of the first embodiment.
FIG. 4 is a top plan view of the first embodiment.
FIG. 5 is a bottom plan view of the first embodiment
FIG. 6 is a side elevational view of the first embodiment.
FIG. 7 is a front elevational view of a second embodiment of the present invention.
FIG. 8 is a rear elevational view of the second embodiment.
FIG. 9 is a top plan view of the second embodiment.
FIG. 10 is a bottom plan view of the second embodiment.
FIG. 11 is a side elevational view of the second embodiment.
FIG. 12 is a side elevational view of a third embodiment of the present invention mounted on the forefinger of a medical practitioner.
FIG. 13 is a rear elevational view of the third embodiment.
FIG. 14 is a front elevational view of the third embodiment.
FIG. 15 is a top plan view of the third embodiment.
FIG. 16 is a side elevational view of the third embodiment.
FIG. 17 is a bottom plan view of the third embodiment.
FIG. 18 is a fragmentary view of the metal protrusions of distal end of the first embodiment and bottom of third embodiments, as illustrated in FIG. 17.
FIG. 19 is a fragmentary view of the distal end of the second embodiment, as illustrated in FIG. 11.

DETAILED DESCRIPTION OF THE INVENTION

Referring generally to the FIGS. 1-6, a first embodiment 10 of the present invention is illustrated A generally cylindrically shaped body 12 has a first or distal end 14 and a second or proximal end 16, and is conformed to be received by a fingertip of a medical practitioner. The body 12 comprises an elongated base 18 and a domed shaped cap 20 defined on the first end 14 of the body 12. The base 18 is composed of metal, preferably stainless steel, and has a generally curvilinear shaped outer surface 22. A plurality of metallic protrusions 34 with sharpened distal ends are integrally formed and positioned along the outer surface 22 of the base 18, and also on an outer surface 24 of the cap 20. An inner panel 26 has a concave inner surface 28 longitudinally extending from the distal end 14 of the body 12 to the proximal end 16 of the body 12. Inwardly depending edges 30 are defined on the periphery of the inner panel 26 along a topmost portion of the base 18. The inner panel 26 and edges 30 are formed of rigid material, such as hard plastic. Straps 32 are disposed and attached to the edges 30, and can be comprised of elastic, plastic, rubber or any other resilient and flexible material. The straps 32 are spaced apart and secure the device 10 to any finger of a medical practitioner. The plastic composition of the inner panel 26 allows for smooth removal from the finger.

As illustrated more fully in FIG. 18, the metallic protrusions 34 extend vertically from the outer surfaces 22, 24 are generally conically shaped with upwardly depending faces 36 defining an open end with an upper sharpened edge 38 for debridement. The sharpened edge of the protrusions 34 are directed towards a scrapping action is all directions. The metallic protrusions 34 are short sharp pieces that facilitate mild debridement in areas not easily accessible by a conventional curette, due to the rigid shape of the curette. The shape of the device 10 allows the practitioner not only to debride shallow areas, but also to debride tunnels and underminings. The metallic protrusions 34 are not limited to any specific configurations, and come in a variety of oriented arrangements, indentations and contact surface prominences.

Referring generally to the FIGS. 7-11, an alternate embodiment 40 of the present invention is illustrated. A generally cylindrically shaped body 42 has a first or distal end 44 and a second or proximal end 46, and is conformed to be received by a fingertip of a medical practitioner. The body 42 comprises an elongated base 48 and a dome shaped cap 50 defined on the first end 44 of the body 42. The base 48 has a generally curvilinear outer surface 52 and an inner panel 54 having a longitudinally groove 56 extending from the second end 46 to the first end 44 of the body 42. Inwardly depending edges 58 are defined on the periphery of the panel 54 along a topmost portion of the base 48. The base 48 is composed of rigid plastic. The cap 50 is composed of stainless steel. Straps are disposed and attached to the edges 30, and can be comprised of elastic, plastic, rubber or any other resilient and flexible material.

A plurality of metallic projections 60 with a sharpened pointed end 66 are integrally formed, and extend vertically from an outer surface 62 of the cap 50. As more fully illustrated in FIG. 19, the projections 60 are generally pyramid shaped with a plurality of parallel faces 64 depending upwardly to the sharpened pointed end 66. The projections 60 are specifically used for cross-hatching techinque in cutting tissue, that is laying down one pass of cuts in one direction and laying down a second set of cuts in perpendicular or near-perpendicular fashion in relation to the first series of cuts. The medical practitioner can cut in multiple directions without limitation. The metallic projections 60 are not limited to any specific configurations, and come in a variety of oriented arrangements, indentations and contact surface prominences.

A semi-circular blade 68 having sharpened edge 70 with a passage defined therethrough 72 depends downwardly from the outer surface 52 of the base 48. The blade 68 is similar to a curette. Straps 74 are disposed and attached to the base 48, and can be comprised of elastic, plastic, rubber or any other resilient and flexible material. The straps 74 are spaced apart and secure the device 40 to any finger of a medical practitioner.

A further alternative embodiment of the invention 80 is illustrated in FIGS. 12-17. A body 82 has a first end 84 and a second end 86. The body 82 comprises an outer panel 88 and an inner panel 90. The outer panel 88 has a generally curvilinear outer surface 92. A platform 94 with metallic protrusions 34 extending vertically is affixed on the outer surface of the outer panel 88. Generally arcuately shaped end edges 96 are defined at the first end 84 and second end 86. Planer side edges 98 are defined on the topmost portion of the body 82. A pair of straps are attached to the body 82, and can be comprised of elastic, plastic, rubber or any other resilient and flexible material.

As illustrated in FIG. 18, and defined in the first embodiment of the invention, the metallic protrusions 34 extending vertically are generally conically shaped with upwardly depending faces 36 defining an open end with an upper sharpened edge 38 for debridement. The sharpened edge of the protrusions 34 are directed towards a scrapping action is all directions.

There has thus been outlined, rather broadly, the more important features of the invention in order that the detailed description thereof that follows may be better understood and in order that the present contribution to the art may be better appreciated. There are, of course, additional features of the invention that will be described hereinafter and which will form the subject matter of the claims attached.

I claim:

1. A medical device for debridement of tissue, comprising in combination:
    a generally cylindrical shaped body having a base, and a cap integrally formed at the distalmost end of the base;
    a plurality of metallic projections, each having a sharpened distal end, extending vertically from an outer surface of the cap;
    a semi-circular blade having a sharpened edge withi a passage defined therethrough depending downwardly from the outer surface of the base; and
    at least one strap attached to the body for circumferential engagement with a finger of a medical practitioner.

2. The device as set forth in claim 1, whereby the projections are generally pyramid shaped with a plurality of parallel faces depending, upwardly.

* * * * *